United States Patent
Shalaby et al.

(10) Patent No.: US 7,070,858 B2
(45) Date of Patent: *Jul. 4, 2006

(54) AMORPHOUS POLYMERIC POLYAXIAL INITIATORS AND COMPLIANT CRYSTALLINE COPOLYMERS THEREFROM

(75) Inventors: Shalaby W. Shalaby, Anderson, SC (US); Torbjorn Mathisen, Stockholm (SE)

(73) Assignee: Poly Med Inc, Anderson, SC (US)

( * ) Notice: Subject to any disclaimer, the term of this patent is extended or adjusted under 35 U.S.C. 154(b) by 343 days.

This patent is subject to a terminal disclaimer.

(21) Appl. No.: 10/630,320

(22) Filed: Jul. 30, 2003

(65) Prior Publication Data

US 2004/0116620 A1     Jun. 17, 2004

Related U.S. Application Data

(60) Division of application No. 10/003,640, filed on Nov. 2, 2001, now abandoned, which is a continuation-in-part of application No. 09/698,527, filed on Oct. 27, 2000, now Pat. No. 6,462,169.

(51) Int. Cl.
C08G 63/08     (2006.01)
C08G 69/08     (2006.01)
A61B 17/00     (2006.01)

(52) U.S. Cl. .......... 428/411.1; 428/480; 428/34.1; 428/36.9; 528/354; 528/355; 528/357; 528/359; 528/361; 528/363; 525/408; 525/411; 525/413; 525/415; 623/1.15; 606/228; 606/229; 606/230; 606/231

(58) Field of Classification Search .......... 428/480, 428/411.1, 34.1, 36.9; 528/354–355, 357–359; 528/361, 363; 525/408, 411, 413, 415, 439; 623/1.15, 1.49; 606/228–231
See application file for complete search history.

(56) References Cited

U.S. PATENT DOCUMENTS

| | | | |
|---|---|---|---|
| 4,429,080 A | 1/1984 | Casey et al. | 525/415 |
| 4,470,416 A | 9/1984 | Kafrawy et al. | 128/335.5 |
| 4,532,928 A | 8/1985 | Bezwada et al. | 128/335.5 |
| 4,543,952 A | 10/1985 | Shalaby et al. | 128/335.5 |
| 4,643,191 A * | 2/1987 | Bezwada et al. | 606/230 |
| 4,916,193 A * | 4/1990 | Tang et al. | 525/413 |
| 5,066,772 A * | 11/1991 | Tang et al. | 528/354 |
| 5,133,739 A | 7/1992 | Bezwada et al. | 606/230 |
| 5,185,408 A * | 2/1993 | Tang et al. | 525/415 |
| 5,236,444 A | 8/1993 | Muth et al. | 606/230 |
| 5,403,347 A | 4/1995 | Roby et al. | 606/230 |
| 5,412,068 A * | 5/1995 | Tang et al. | 528/370 |
| 5,431,679 A | 7/1995 | Bennett et al. | 606/230 |
| 5,468,253 A | 11/1995 | Bezwada et al. | 606/228 |
| 5,554,170 A | 9/1996 | Roby et al. | 606/230 |
| 5,620,461 A | 4/1997 | Muijs Van De Moer et al. | 606/213 |
| 5,644,002 A | 7/1997 | Cooper et al. | 525/411 |
| 5,713,920 A | 2/1998 | Bezwada et al. | 606/230 |
| 6,462,169 B1 * | 10/2002 | Shalaby | 528/354 |
| 6,794,485 B1 * | 9/2004 | Shalaby et al. | 528/354 |
| 2005/0171299 A1 * | 8/2005 | Shalaby | 525/437 |

FOREIGN PATENT DOCUMENTS

| | | |
|---|---|---|
| EP | 0 618 250 A1 | 3/1994 |
| EP | 0 697 427 A2 | 7/1995 |
| EP | 0 712 880 A2 | 11/1995 |
| EP | 0 737 703 A2 | 4/1996 |

OTHER PUBLICATIONS

Correa et al., Sixth World Biomaterials Congress, *Trans So.c Biomat., II*, 992 (2000).
L. Mandelkern, *Crystallization of Polymers*, McGraw-Hill Book Company, NY, 1964, p. 105-106.
S.W. Shalaby, Chapter 3 of *Thermal Characterization of Polymeric Materials* (E.A. Tur ed.) Academic Press, NY, 1981, p. 330.
S.W. Shalaby and H.E. Blair, Chapter 4 of *Thermal Characterization of Polymeric Materials* (E.A. Turi ed.) Academic Press, NY, 1981, p. 402.

* cited by examiner

Primary Examiner—P. Hampton Hightower
(74) Attorney, Agent, or Firm—Leigh P Gregory

(57) ABSTRACT

An absorbable crystalline, monocentric polyaxial copolymer comprising a central carbon or nitrogen atom and at least three axes, each of which includes an amorphous flexible component adjacent and originating from the central atom and a rigid, crystallizable component extending outwardly from the amorphous, flexible component is disclosed along with the use of such copolymer in medical devices which may contain a bioactive agent. The present invention also relates to a suture, stents, stent mantles and sealing devices made from the polyaxial copolymer.

7 Claims, 3 Drawing Sheets

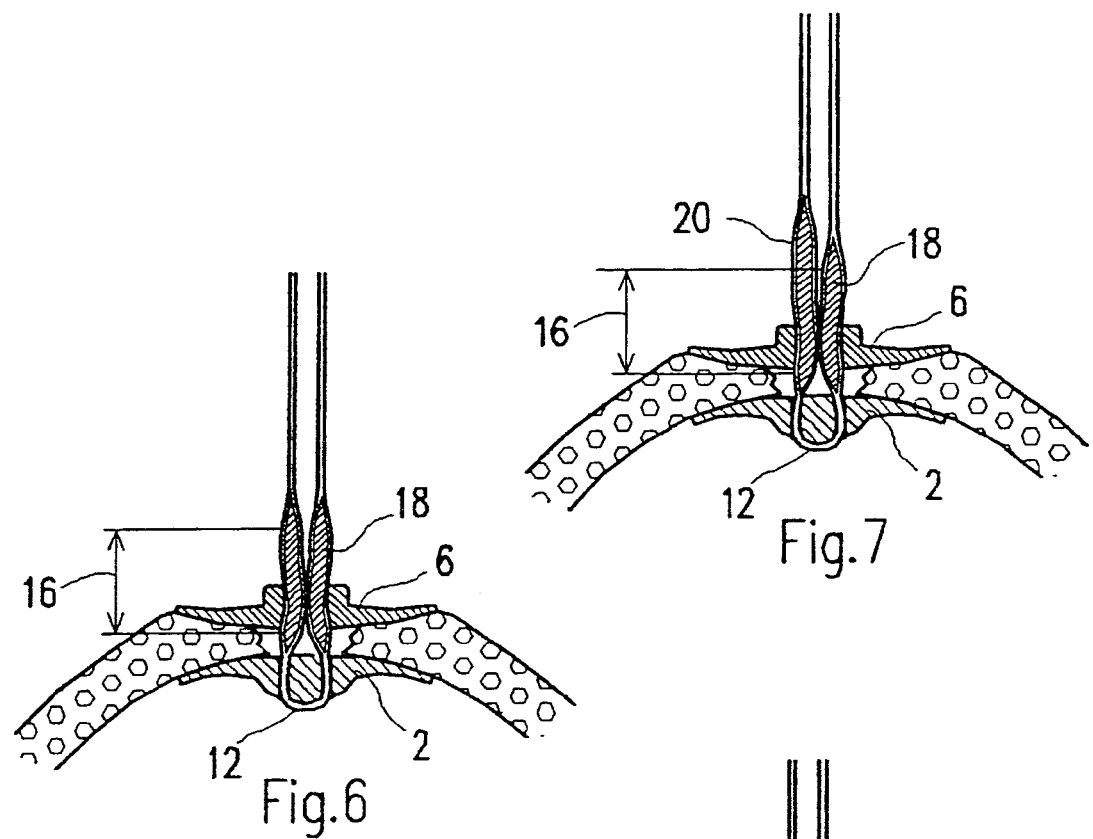
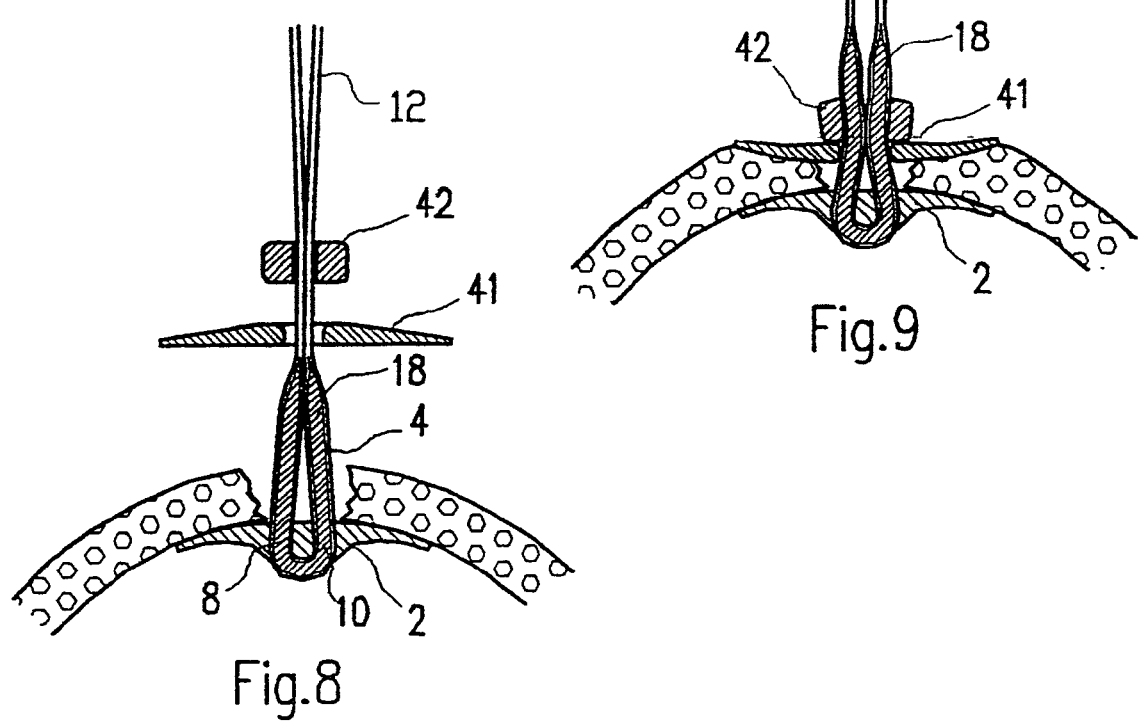

AMORPHOUS POLYMERIC POLYAXIAL INITIATORS AND COMPLIANT CRYSTALLINE COPOLYMERS THEREFROM

This is a divisional application of U.S. Ser. No. 10/003,640, filed Nov. 2, 2001, now abandoned which is a continuation-in-part of U.S. Ser. No. 09/698,527, filed Oct. 27, 2000, now U.S. Pat. No. 6,462,169.

BACKGROUND OF THE INVENTION

Since the successful development of crystalline thermoplastic polyglycolide as an absorbable fiber-forming material, there has been a great deal of effort directed to the development of new linear fiber-forming polyesters with modulated mechanical properties and absorption profiles. Such modulation was made possible through the application of the concept of chain segmentation or block formation, where linear macromolecular chains comprise different chemical entities with a wide range of physicochemical properties, among which is the ability to crystallize or impart internal plasticization. Typical examples illustrating the use of this strategy are found in U.S. Pat. Nos. 5,554,170, 5,431,679, 5,403,347, 5,236,444, and 5,133,739, where difunctional initiators were used to produce linear crystallizable copolymeric chains having different microstructures.

On the other hand, controlled branching in crystalline, homochain polymers, such as polyethylene, has been used as a strategy to broaden the distribution in crystallite size, lower the overall degree in crystallinity and increase compliance (L. Mandelkern, *Crystallization of Polymers*, McGraw-Hill Book Company, NY, 1964, p. 105–106). A similar but more difficult-to-implement approach to achieving such an effect on crystallinity as alluded to above has been used specifically in the production of linear segmented and block heterochain copolymers such as (1) non-absorbable polyether-esters of polybutylene terephthalate and polytetramethylene oxide [see S. W. Shalaby and H. E. Bair, Chapter 4 of *Thermal Characterization of Polymeric Materials* (E.A. Turi, Ed.) Academic Press, NY, 1981, p. 402; S. W. Shalaby et al., U.S. Pat. No. 4,543,952 (1985)]; (2) block/segmented absorbable copolymers of high melting crystallizable polyesters Such as polyglycolide with amorphous polyether-ester such as poly-1,5-dioxepane-2-one (see A. Kafrawy et al., U.S. Pat. No. 4,470,416 (1984)); and (3) block/segmented absorbable copolyesters of crystallizable and non-crystallizable components as cited in U.S. Pat. Nos. 5,554,170, 5,431,679, 5,403,347, 5,236,444, and 5,133,739. However, the use of a combination of controlled branching (polyaxial chain geometry) and chain segmentation or block formation of the individual branches to produce absorbable polymers with tailored properties cannot be found in the prior art. This and recognized needs for absorbable polymers having unique combinations of crystallinity and high compliance that can be melt-processed into high strength fibers and films with relatively brief absorption profiles as compared to their homopolymeric crystalline analogs provided an incentive to explore a novel approach to the design of macromolecular chains to fulfill such needs. Meanwhile, initiation of ring-opening polymerization with organic compounds having three or four functional groups have been used as a means to produce crosslinked elastomeric absorbable systems as in the examples and claims of U.S. Pat. No. 5,644,002. Contrary to this prior art and in concert with the recognized needs for novel crystallizable, melt-processable materials, the present invention deals with the synthesis and use of polyaxial initiators with three or more functional groups to produce crystallizable materials with melting temperatures above 100° C., which can be melt-processed into highly compliant absorbable films and fibers.

SUMMARY OF THE INVENTION

In one aspect the present invention is directed to an absorbable, crystalline, monocentric, polyaxial copolymer which includes a central atom which is carbon or nitrogen and at least three axes originating and extending outwardly from the central atom, each axis including an amorphous, flexible component adjacent to and originating from the central atom, the amorphous component being formed of repeat units derived from at least one cyclic monomer, either a carbonate or a lactone, and a rigid, crystallizable component extending outwardly from the amorphous, flexible component, the crystallizable component being formed of repeat units derived from at least one lactone, wherein the copolymer comprises a melting temperature greater than 120° C., a heat of fusion greater than 10 J/g, and an endothermic transition at 40–100° C., wherein the endothermic transition can be controlled by subsequent heat treatment, such as orientation or annealing, of the copolymer. In one embodiment, a composite cover or mantle for a stent which includes a polymeric matrix reinforced with monofilament cross-spirals may be provided wherein the matrix, the monofilaments or both may be made of the copolymer of the present invention.

The flexible polyaxial initiator can be derived from p-dioxanone, 1,5-dioxepan-2-one, or one of the following mixtures of polymers: (1) trimethylene carbonate and 1,5-dioxepan-2-one with or without a small amount of glycolide; (2) trimethylene carbonate and a cyclic dimer of 1,5-dioxepan-2-one with or without a small amount of glycolide; (3) caprolactone and p-dioxanone with or without a small amount of glycolide; (4) trimethylene carbonate and caprolactone with or without a small amount of dl-lactide; (5) caprolactone and dl-lactide with or without a small amount of glycolide; and (6) trimethylene carbonate and dl-lactide with or without a small amount of glycolide. Further, the crystallizable segment can be derived from glycolide or 1-lactide. Alternate precursors of the crystallizable segment can be a mixture that is predominantly glycolide or 1-lactide with a minor component of one or more of the following monomers: p-dioxanone, 1,5-dioxepan-2-one, trimethylene carbonate, and caprolactone.

In another embodiment the present invention is directed to a device for sealing a puncture in a blood vessel, which includes a first flexible sealing member, which is positionable inside the blood vessel immediately adjacent to the puncture; an elongated member which is a composite and has an axial direction, a cross-sectional diameter, a proximal end and a distal end, wherein the first sealing member is attached to the distal end of the elongated member, the elongated member is capable of positioning the first sealing member within the blood vessel and immediately adjacent to the puncture, the elongated member further includes a distal locking portion comprising an enlarged cross-sectional diameter at the distal portion which extends outwardly from the punctured blood vessel when the first sealing member is positioned within the blood vessel and immediately adjacent to the puncture; and a second flexible sealing member threadable onto the elongated member by an opening defined therein, the second sealing member comprising locking means for locking onto the distal locking portion of the elongated member, such that the second sealing means is locked onto the elongated member on the outside of the blood vessel immediately adjacent to the puncture thereby sealing the puncture. Preferably, the locking means of the second sealing member comprises the opening defined therein having a diameter less than the enlarged cross-sectional diameter of the distal locking portion of the elongated member such that the second flexible sealing member is capable of stretching the opening defined therein for frictional engagement with the distal locking portion of the elongated member. Alternatively, the locking means of the second sealing member is a further flexible member threadable onto the elongated member having an opening defined therein which has a diameter less than the enlarged cross-sectional diameter of the distal locking portion of the elongated member, the further flexible member being capable of stretching the opening defined therein for frictional engagement with the distal locking portion of the elongate member, wherein the further flexible member is locked immediately adjacent to the second sealing member and opposite to the puncture of the blood vessel.

Preferably, either the first sealing member, the second sealing member or both is a formed from an absorbable polymer. Most preferably, at least one of the first sealing member and the second sealing member comprise an absorbable, crystalline, monocentric, polyaxial copolymer which includes a central atom selected from the group consisting of carbon and nitrogen; and at least three axes originating and extending outwardly from the central atom, each axis including: an amorphous, flexible component adjacent to and originating from the central atom, the amorphous component consisting of repeat units derived from at least one cyclic monomer selected from the group consisting essentially of carbonates and lactones; and a rigid, crystallizable component extending outwardly from the amorphous, flexible component, the crystallizable component consisting of repeat units derived from at least one lactone.

Preferably, the elongated member comprises a composite of a highly flexible sheath and a less flexible solid, monofilament core, the less flexible core within the sheath comprising the enlarged cross-sectional diameter of the distal locking portion of the elongated member composite. It is preferred that the sheath is a braided suture and the less flexible filament is threaded through the interior portion of the suture. It is also preferred that the ends of the filament are tapered. In one embodiment the less flexible filament is sufficiently flexible to compress and frictionally engage the opening defined within the second sealing member.

According to still another aspect of the present invention the subject copolymer is converted to different forms of absorbable stents, a tubular mantle (or cover) for stents, sutures, sealing devices or parts of multicomponent sealing devices for closing (or plugging) a wound or a needle hole in a wall of a blood vessel.

BRIEF DESCRIPTION OF THE DRAWINGS

The foregoing and other aspects of the present invention will be best appreciated with reference to the following detailed description of specific embodiments of the invention, given by way of example only, when read in conjunction with the accompanying drawing, wherein

FIG. 6 shows a sealing device for closing a wound in a wall of a vessel according to a second embodiment of a first specific application of the invention;

FIG. 7 shows a sealing device for closing a wound in a wall of a vessel according to a third embodiment of a first specific application of the invention;

FIG. 8 shows a sealing device for closing a wound in a wall of a vessel according to a fifth embodiment of a first specific application of the invention;

FIG. 9 shows a sealing device for closing a wound in a wall of a vessel according to a fifth embodiment of a first specific application of the invention;

DETAILED DESCRIPTION OF PREFERRED EMBODIMENTS

Figure 1:
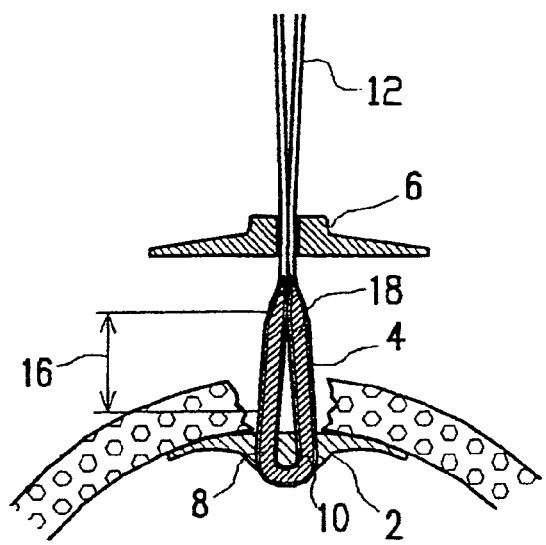
FIG. 1 shows a sealing device for closing a wound in a wall of a vessel according to a first embodiment of a first specific application of the invention.

This invention deals with absorbable, polyaxial, monocentric, crystallizable, polymeric molecules with non-crystallizable, flexible components of the chain at the core and rigid, crystallizable segments at the chain terminals. More specifically, the present invention is directed to the design of amorphous polymeric polyaxial initiators with branches originating from one polyfunctional organic compound so as to extend along more than two coordinates and their copolymerization with cyclic monomers to produce compliant, crystalline film- and fiber-forming absorbable materials. The absorbable copolymeric materials of this invention comprise at least 30 percent, and preferably 65 percent, by weight, of a crystallizable component which is made primarily of glycolide-derived or l-lactide-derived sequences, and exhibit first and second order transitions below 222° C. and below 42° C., respectively, and undergo complete dissociation into water-soluble by-products in less than eighteen months and preferably less than twelve months, and more preferably less than six months, and much more preferably less than four months when incubated in a phosphate buffer at 37° C. and pH 7.4 or implanted in living tissues.

The amorphous polymeric, polyaxial initiators (PPIs) used in this invention to produce crystalline absorbable copolymeric materials can be made by reacting a cyclic monomer or a mixture of cyclic monomers such as trimethylene carbonate, caprolactone, and 1,5-dioxapane-2-one in the presence of an organometallic catalyst with one or more polyhydroxy, polyamino, or hydroxyamino compound having three or more reactive amines and/or hydroxyl groups. Typical examples of the latter compounds are glycerol and ethane-trimethylol, propane-trimethylol, pentaerythritol, triethanolamine, and N-2-aminoethyl-lactide 1,3-propanediamine.

The flexible polyaxial initiator can be derived from p-dioxanone, 1,5-dioxepan-2-one, or one of the following mixtures of polymers: (1) trimethylene carbonate and 1,5-dioxepan-2-one with or without a small amount of glycolide;

(2) trimethylene carbonate and a cyclic dimer of 1,5-dioxepan-2-one with or without a small amount of glycolide; (3) caprolactone and p-dioxanone with or without a small amount of glycolide; (4) trimethylene carbonate and caprolactone with or without a small amount of dl-lactide; (5) caprolactone and dl-lactide (or meso-lactide) with or without a small amount of glycolide; and (6) trimethylene carbonate and dl-lactide (or meso-lactide) with or without a small amount of glycolide. Further, the crystallizable segment can be derived from glycolide or 1-lactide. Alternate precursors of the crystallizable segment can be a mixture of predominantly glycolide or 1-lactide with a minor component of one or more of the following monomers: p-dioxanone, 1,5-dioxepan-2-one, trimethylene carbonate, and caprolactone.

The crystalline copolymers of the present invention are so designed to (1) have the PPI devoid of any discernable level of crystallinity; (2) have the PPI component function as a flexible spacer of a terminally placed, rigid, crystallizable component derived primarily from glycolide so as to allow for facile molecular entanglement to create pseudo-crosslinks, which in turn, maximize the interfacing of the amorphous and crystalline fractions of the copolymer leading to high compliance without compromising tensile strength; (3) maximize the incorporation of the hydrolytically labile glycolate linkage in the copolymer without compromising the sought high compliance—this is achieved by directing the polyglycolide segments to grow on multiple active sites of the polymeric initiator and thus limiting the length of the crystallizable chain segments; (4) have a broad crystallization window featuring maximum nucleation sites and slow crystallite growth that in turn assists in securing a highly controlled post-processing and development of mechanical properties—this is achieved by allowing the crystallizable components to entangle effectively with non-crystallizable components leading to high affinity for nucleation, high pre-crystallization viscosity, slow chain motion, and low rate of crystallization; (5) force the polymer to form less perfect crystallites with broad size distribution and lower their melting temperature as compared to their homopolymeric crystalline analogs to aid melt-processing—this is achieved by limiting the length of the crystallizable segments of the copolymeric chain as discussed earlier; (6) allow for incorporating basic moieties in the PPI which can affect autocatalytic hydrolysis of the entire system which in turn accelerates the absorption rate; and (7) allow the polymer chain to associate so as to allow for endothermic thermal events to take place between 40 and 100° C. that can be associated with an increase in tensile toughness similar to that detected in PET relative to the so-called middle endothermic peak (MEP) (S. W. Shalaby, Chapter 3 of *Thermal Characterization of Polymeric Materials*, Academic press, NY, 1981, p. 330). The temperature at which these transitions take place is dependent on the degree of orientation of the polymers of this invention and the temperatures at which the polymers are annealed.

As an example, the crystalline copolymeric materials of the present invention may be prepared as follows, although as noted above, other monomers are also within the scope of the present invention. The amorphous polymeric polyaxial initiator is formed by a preliminary polymerization of a mixture of caprolactone and trimethylene carbonate in the presence of trimethylol-propane and a catalytic amount of stannous octoate, using standard ring-opening polymerization conditions which entail heating the stirred reactants in nitrogen atmosphere at a temperature exceeding 110° C. until substantial or complete conversion of the monomers is realized. This can be followed by adding a predetermined amount of glycolide. Following the dissolution of the glycolide in the reaction mixture, the temperature is raised above 150° C. but not to exceed 180° C. for more than 30 minutes to allow the glycolide to copolymerize with the polyaxial initiator without compromising the expected sequence distribution in PPI and the microtexture of the crystallizable terminal. When practically all the glycolide is allowed to react, the resulting copolymer is cooled to 25° C. After removing the polymer from the reaction kettle and grinding, trace amounts of unreacted monomer are removed by heating under reduced pressure. The ground polymer can then be extruded and pelletized prior to its conversion to fibers or films by conventional melt-processing methods. At the appropriate stage of polymerization and product purification, traditional analytical methods, such as gel-permeation chromatography (GPC), solution viscosity, differential scanning calorimetry (DSC), nuclear magnetic resonance (NMR), and infrared spectroscopy (IR) are used to monitor or determine (directly or indirectly) the extent of monomer conversion, molecular weight, thermal transitions (melting temperature, Tm, and glass transition temperature, Tg), chain microstructure, and chemical entity, respectively.

Another aspect of this invention deals with end-grafting a PPI with caprolactone or 1-lactide, and preferably in the presence of a minor amount of a second monomer, to produce absorbable crystalline polymers for use as bone sealants, barrier membranes, thin films, or sheets. The latter three can be made to have continuous cell microporous morphology.

Films made by compression molding of the copolymers described in the examples set forth below are evaluated for (1) tensile strength; (2) in vitro breaking strength retention and mass loss during incubation in a phosphate buffer at 37° C. and pH 7.4; (3) in vivo breaking strength retention using a rat model where strips of the films are implanted subcutaneously for 1 to 6 weeks and individual lengths are explanted periodically to determine percent of retained breaking strength; and (4) in vivo absorption (in terms of mass loss) using a rat model where a film strip, inserted in a sealed polyethylene terephthalate (PET) woven bag, is placed in the peritoneum for 6, 8, 10, 12 and 14 weeks. At the end of each period, the PET bag is removed and the residual mass of the strips is removed, rinsed with water, dried, and its weight is determined.

Specifically, an important aspect of this invention is the production of compliant absorbable films with modulated absorption and strength loss profiles to allow their use in a wide range of applications as vascular devices or components therefor. More specifically is the use of these devices in sealing punctured blood vessels.

In another aspect, this invention is directed to the use of the polymers described herein for the production of extruded or molded films for use in barrier systems to prevent post-surgical adhesion or compliant covers, sealants, or barriers for burns and ulcers as well as compromised/damaged tissue. The aforementioned articles may also contain one or more bioactive agent to augment or accelerate their functions. In another aspect, this invention is directed to melt-processed films for use to patch mechanically compromised blood vessels. In another aspect, this invention is directed to the use of the polymer described herein as a coating for intravascular devices such as catheters and stents. In another aspect, this invention is directed to the application of the polymers described herein in the production of extruded catheters for use as transient conduits and microcellular foams with continuous porous structure for use in tissue engineering and guiding the growth of blood vessels and nerve ends. Another aspect of this invention is directed to the use of the polymers described herein to produce injection molded articles for use as barriers, or plugs, to aid the function of certain biomedical devices used in soft and hard tissues and which can be employed in repairing, augmenting, substituting or redirecting/assisting the functions of several types of tissues including bone, cartilage, and lung as well as vascular tissues and components of the gastrointestinal and urinogenital systems. In another aspect, this invention is directed to the use of polymers described herein to produce compliant, melt-blown fabrics and monofilament sutures with modulated absorption and strength retention profiles.

In one aspect of this invention, the subject copolymers are converted to different forms of absorbable stents, such as those used (1) as an intraluminal device for sutureless gastrointestinal sutureless anastomosis; (2) in laparoscopic replacement of urinary tract segments; (3) as an intraluminal device for artery welding; (4) in the treatment of urethral lesions; (5) as a tracheal airway; (6) in the treatment of recurrent urethral strictures; (7) for vasectomy reversal; (8) in the treatment of tracheal stenoses in children; (9) for vasovasostomy; (10) for end-to-end ureterostomy; and (11) as biliary devices.

In another aspect of this invention, the subject copolymers are converted to a highly compliant, expandable tubular mantle, sleeve or cover that is placed tightly outside an expandable metallic or polymeric stent so that under concentric irreversible expansion at the desired site of a treated biological conduit, such as blood vessel or a urethra, both components will simultaneously expand and the mantle provides a barrier between the inner wall of the conduit and the outer wall of the stent. In another aspect of this invention, the subject copolymers are used as a stretchable matrix of a fiber-reinforced cover, sleeve, or mantle for a stent, wherein the fiber reinforcement is in the form of spirally coiled yarn (with and without crimping) woven, knitted, or braided construct. In another aspect of this invention, the stent mantle, or cover, is designed to serve a controlled release matrix of bioactive agents such as those used (1) for inhibiting neointima formation as exemplified by hirudin and the prostacyclic analogue, iloprost; (2) for inhibiting platelet aggregation and thrombosis; (3) for reducing intraluminal and particular intravascular inflammation as exemplified by dexamethasone and non-steroidal inflammatory drugs, such as naproxen; and (4) for suppressing the restenosis.

One aspect of this invention deals with the conversion of the subject copolymers into molded devices or components of devices used as a hemostatic puncture closure device after coronary angioplasty.

It is further within the scope of this invention to incorporate one or more medico-surgically useful substances into the copolymers and devices subject of this invention. Typical examples of these substances are those capable of (1) minimizing or preventing platelet adhesion to the surface of vascular grafts; (2) rendering anti-inflammatory functions; (3) blocking incidents leading to hyperplasia as in the case of synthetic vascular grafts; (4) aiding endothelialization of synthetic vascular grafts; (5) preventing smooth muscle cell migration to the lumen of synthetic vascular grafts; and (6) accelerating guided tissue ingrowth in fully or partially absorbable scaffolds used in vascular tissue engineering.

In order that those skilled in the art may be better able to practice the present invention, the following illustrations of the preparation of typical crystalline copolymers are provided.

EXAMPLE 1

Synthesis of 20/25 (Molar)
Caprolactone/Trimethylene Carbonate Copolymer
as a Triaxial Initiator and Reaction with 55
Relative Molar Parts of Glycolide An initial charge consisted of 142.4 grams (1.249 moles) caprolactone, 159.4 grams (1.563 moles) trimethylene carbonate, 1.666 grams ($1.24 \times 10^{-2}$ moles) trimethylol-propane, and 1.0 ml ($2.03 \times 10^{-4}$ moles) of a 0.203M solution of stannous octoate catalyst in toluene after flame drying the reaction apparatus. The reaction apparatus was a 1 L stainless steel kettle with 3-neck glass lid equipped with an overhead mechanical stirring unit, vacuum adapter, and two 90° connectors for an argon inlet.

The apparatus and its contents were heated to 50° C. under vacuum with a high temperature oil bath. Upon complete melting of the contents after 30 minutes, the system was purged with argon, stirring initiated at 32 rpm, and the temperature set to 150° C. After 4 hours at 150° C., the viscosity of the polyaxial polymeric initiator (PPI) had increased and the temperature of the bath was reduced to 110° C. Upon reaching 110° C., 398.5 grams (3.435 moles) of glycolide were added to the system. When the glycolide had completely melted and mixed into the polyaxial polymeric initiator, the temperature was increased to 180° C. and stirring was stopped. The reaction was allowed to continue for 2 hours before cooling the system to 50° C. and maintaining the heat overnight. The polymer was isolated, ground, dried, extruded and redried as described below in Example 5.

The extrudate was characterized as follows: The inherent viscosity using hexafluoroisopropyl alcohol (HFIP) as a solvent was 0.97 dL/g. The melting temperature and heat of fusion, as determined by differential scanning calorimetry (using initial heating thermogram), were 215° C. and 40.8 J/g, respectively.

EXAMPLE 2

Synthesis of 25/30 (Molar)
Caprolactone/Trimethylene Carbonate Copolymer
as a Triaxial Initiator and Reaction with 45
Relative Molar Parts of Glycolide An initial charge consisted of 122.8 grams (1.077 moles) caprolactone, 131.9 grams (1.292 moles) trimethylene carbonate, 1.928 grams ($1.44 \times 10^{-2}$ moles) trimethylol-propane, and 1.0 ml ($8.62 \times 10^{-5}$ moles) of a 0.086M solution of stannous octoate catalyst in toluene after flame drying the reaction apparatus. The reaction apparatus was a 1 L stainless steel kettle with 3-neck glass lid equipped with an overhead mechanical stirring unit, vacuum adapter, and two 90° connectors for an argon inlet.

The apparatus and its contents were then heated to 65° C. under vacuum with a high temperature oil bath. After 30 minutes, with the contents completely melted, the system was purged with argon, stirring initiated at 34 rpm, and the temperature set to 140° C. After 3 hours at 140° C., the temperature was raised to 150° C. for 1 hour and then reduced back to 140° C. At this point, 225.0 grams (1.940 moles) of glycolide were added to the system while rapidly stirring. When the glycolide had completely melted and mixed into the polyaxial polymeric initiator, the temperature was increased to 180° C. and stirring was stopped. The reaction was allowed to continue for 2 hours before cooling the system to room temperature overnight. The polymer was isolated, ground, dried, extruded, and redried as described in Example 5.

Characterization of the extrudate was conducted as follows: The inherent viscosity using HFIP as a solvent was 0.93 dL/g. The melting temperature and heat of fusion, as measured by differential scanning calorimetry (DSC using initial heating thermogram), were 196° C. and 32.1 J/g, respectively.

EXAMPLE 3

Synthesis of 20/25/3 (Molar) Caprolactone/Trimethylene Carbonate/Glycolide Copolymer as a Triaxial Initiator and Reaction with 52 Relative Molar Parts of Glycolide An initial charge consisted of 101.6 grams (0.891 moles) caprolactone, 113.5 grams (1.113 moles) trimethylene carbonate, 15.5 grams of glycolide (0.134 moles), 1.996 grams ($1.49 \times 10^{-2}$ moles) trimethylol-propane, and 1.0 ml ($1.28 \times 10^{-4}$ moles) of a 0.128M solution of stannous octoate catalyst in toluene after flame drying the reaction apparatus. The reaction apparatus was a 1 L stainless steel kettle with 3-neck glass lid equipped, an overhead mechanical stirring unit, vacuum adapter, and two 90° connectors for an argon inlet.

The apparatus and its contents were then heated to 85° C. under vacuum with a high temperature oil bath. After 30 minutes, with the contents completely melted, the system was purged with argon, stirring initiated at 34 rpm, and the temperature set to 140° C. After 4 hours at 140° C., 268.8 grams (2.317 moles) of glycolide were added to the system while rapidly stirring. When the glycolide had completely melted and mixed into the polyaxial polymeric initiator, the temperature was increased to 180° C. and stirring was stopped. The reaction was allowed to continue for 2 hours before cooling the system to room temperature overnight. The polymer was isolated, ground, dried, extruded and redried as in Example 5.

The extrudate was characterized as follows: The inherent viscosity using HFIP as a solvent was 0.89 dL/g. The melting temperature and heat of fusion, as measured by differential scanning calorimetry (DSC using initial heating thermogram), were 212° C. and 34 J/g, respectively.

EXAMPLE 4

Synthesis of 20/25/3 (Molar) Caprolactone/Trimethylene-Carbonate/Glycolide Copolymer as a Triaxial Initiator and Reaction with 52 Relative Molar Parts of Glycolide Glycolide (18.6 g, 0.1603 mole), TMC (136.7 g, 1.340 mole), caprolactone (122.0 g, 1.070 mole), trimethylolpropane (2.403 g, 0.01791 mole) and stannous octoate catalyst (0.2M in toluene, 764 µL, 0.1528 mmol) were added under dry nitrogen conditions to a 1.0 liter stainless steel reaction kettle equipped with a glass top and a mechanical stirrer. The reactants were melted at 85° C. and the system was evacuated with vacuum. The system was purged with dry nitrogen and the melt was heated to 160° C. with stirring at 30 rpm. Samples of the prepolymer melt were taken periodically and analyzed for monomer content using GPC. Once the monomer content of the melt was found to be negligible, glycolide (322.5 g, 2.780 mole) was added with rapid stirring. The stir rate was lowered to 30 rpm after the contents were well mixed. The melt was heated to 180° C. Stirring was stopped upon solidification of the polymer. The polymer was heated for 2 hours at 180° C. after solidification. The resulting polymer was cooled to room temperature, quenched in liquid nitrogen, isolated, and dried under vacuum. The polymer was isolated, ground, redried, and extruded as described in Example 5. The extrudate was characterized by NMR and IR for identity and DSC (using initial heating thermogram) for thermal transition ($T_m$=208° C., $\Delta H$=28.0 J/g) and solution viscosity in hexafluoroisopropyl alcohol ($\eta$=0.92 dL/g).

EXAMPLE 5

Size Reduction and Extrusion of Polymers of Examples 1 through 4

The polymer was quenched with liquid nitrogen and mechanically ground. The ground polymer was dried under vacuum at 25° C. for two hours, at 40° C. for two hours, and at 80° C. for four hours. The polymer was melt extruded at 225° C. to 235° C. using a ½ inch extruder equipped with a 0.094 in die. The resulting filaments were water cooled. The average filament diameter was 2.4 mm. The filament was dried at 40° C. and 80° C. under vacuum for eight and four hours, respectively.

EXAMPLE 6

Compression-Molding of Polymers from Examples 3 and 4 to a Sealing Device for a Punctured Blood Vessel and Its Packaging The compression molding process entailed exposing the polymer to an elevated temperature between two mold halves. When temperature of the mold halves exceeded the polymer melting temperature, pressure was applied to the mold and the material was allowed to flow into a predefined cavity of the mold. The mold was then cooled to room temperature before it was opened and the newly shaped polymer was removed.

The full molding cycle can be described as: (1) Drying—typical: temperature 80° C. during 2 hours; (2) Pre-heating, temperature increase—typical: pressure 5,000N, temperature from room temperature up to 200° C.; (3) Forming, constant temperature under high pressure—typical: pressure 50,000N, temperature 200° C.; (4) Cooling, temperature decrease under high pressure—typical: pressure 50,000N, temperature from 200° C. down to 50° C.; (5) Mold opening; (6) Annealing—typical: temperature 80° C. during 2 hours; and (7) Packaging—typically the device was removed from the mold and packaged under vacuum under a protective gas environment.

EXAMPLE 7

Synthesis of 13.3/17.7/2 (Molar) Caprolactone/Trimethylene Carbonate/Glycolide Copolymer as a Triaxial Initiator and Reaction with Relative 67 Molar Parts of Glycolide Glycolide (10.4 g, 0.090 mole), TMC (76.5 g, 0.750 mole), caprolactone (68.4 g, 0.600 mole), trimethylolpropane (1.995 g, 0.01487 mole) and stannous octoate catalyst (0.2M in toluene, 637 μL, 0.1274 mmole) were added under dry nitrogen conditions to a 1.0 liter stainless steel reaction kettle equipped with a glass top and a mechanical stirrer. The reactants were melted at 85° C. and the system was evacuated with vacuum. The system was purged with dry nitrogen and the melt was heated to 160° C. with stirring at 30 rpm. Samples of the prepolymer melt were taken periodically and analyzed for monomer content using GPC. Once the monomer content of the melt was found to be negligible, glycolide (344.5 g, 2.970 mole) was added with rapid stirring. The stir rate was lowered to 30 rpm after the contents were well mixed. The melt was heated to 180° C. Stirring was stopped upon solidification of the polymer. The polymer was heated for 2 hours at 180° C. after solidification. The resulting polymer was cooled to room temperature, quenched in liquid nitrogen, isolated, and dried under vacuum. The polymer was characterized by NMR and IR (for identity), DSC thermal transition ($T_m$=215.7) and solution viscosity in hexafluoroisopropyl alcohol (η–0.95 dL/g).

EXAMPLE 8

Synthesis of 13.6/17.0/2.0 (Molar) Caprolactone/Trimethylene Carbonate/Glycolide Copolymer as a Basic Triaxial Initiator and Reaction with Relative 67.4 Molar Parts of Glycolide and Trimethylene Carbonate Glycolide (3.1 g, 0.0267 mole), TMC (23.0 g, 0.2255 mole), caprolactone (20.5 g, 0.1798 mole), triethanolamine (0.6775 g, 4.55 mmole) and stannous octoate catalyst (0.2M in toluene, 519 μL, 0.1038 mmole) were added under dry nitrogen conditions to a 0.5 Liter stainless steel reaction kettle equipped with a glass top and a mechanical stirrer. The reactants were melted at 85° C. and the system was evacuated with vacuum. The system was purged with dry nitrogen and the melt was heated to 160° C. with stirring at 30 rpm. Samples of the prepolymer melt were taken periodically and analyzed for monomer content using GPC. Once the monomer content of the melt was found to be negligible, glycolide (103.4 g, 0.8914 mole) was added with rapid stirring. The stir rate was lowered to 30 rpm after the contents were well mixed. The melt was heated to 180° C. Stirring was stopped upon solidification of the polymer. The polymer was heated for 2 hours at 180° C. after solidification. The resulting polymer was cooled to room temperature, quenched in liquid nitrogen, isolated, and dried under vacuum. The polymer was characterized for identity and composition (IR and NMR, respectively) and thermal transition by DSC ($T_m$220° C.) and molecular weight by solution viscometry (η=0.80 in hexafluoroisopropyl alcohol).

EXAMPLE 9

Synthesis of 13.6/17.0/2.0 (Molar) Caprolactone/Trimethylene Carbonate/Glycolide Copolymer as a Basic Triaxial Initiator and Reaction with Relative 67.4 Molar Parts of Glycolide The two-step polymerization was conducted as in Example 8 with the exception of using 0.6915 g triethanolamine and 693 μl of stannous octanoate solution. The final polymer was isolated and characterized as in Example 8 and it was shown to have a $T_m$=221° C. and inherent viscosity (in HFIP)=0.82.

EXAMPLE 10

Synthesis of 13.3/17.7/2 (Molar) Caprolactone/Trimethylene Carbonate/Glycolide Copolymer as a Tetra-axial Initiator and Reaction with Relative 67 Molar Parts of Glycolide Glycolide (3.1 g, 0.0267 mole), TMC (23.0 g, 0.2255 mole), caprolactone (20.5. g, 0.1796 mole), pentaerythritol (0.600 g., 0.0044 mole) and stannous octoate catalyst (0.2 M in toluene, 193 μl, 0.0386 mmol) were placed under dry nitrogen conditions to a 0.5 L stainless steel reaction kettle equipped with a glass top and a mechanical stirrer. The polymerization charge was dried at 25° C. and 40° C. under reduced pressure for 60 and 30 minutes, respectively. The reactants were then melted at 85° C. and the system was purged with dry nitrogen. The melt was heated to 160° C. with stirring at 30 rpm. Samples of the prepolymer melt were taken periodically and analyzed for monomer content using GPC (gel permeation chromatography). Once the monomer content of the polymer melt was found to be negligible, glycolide (103.4 g., 0.8914 mole) was added with rapid stirring that is more than 40 rpm. The stirring rate was then lowered to 30 rpm after the contents were well mixed. The reactants were heated to 180° C. Stirring was stopped upon solidification of the polymer. The polymer was heated for 2 hours at 180° C. after solidification. The resulting polymer was cooled to room temperature, quenched in liquid nitrogen, isolated, and dried at 25° C. and then 40° C. under reduced pressure.

The final polymer was isolated and characterized as in Example 8 and it was shown to have a $T_m$=219° C. and inherent viscosity (in HFIP)=0.98.

EXAMPLE 11

Size Reduction and Extrusion of Polymer from Examples 7 through 10

The polymer was quenched with liquid nitrogen and mechanically ground. The ground polymer was dried under vacuum at 25° C. for two hours, at 40° C. for two hours, and at 80° C. for four hours. The polymer was melt extruded at 235° C. to 245° C. using a ½ inch extruder equipped with a 0.094 in die. The resulting monofilament was quenched in an ice-water bath before winding. The monofilament was dried at 40° C. and under vacuum for four hours before orientation.

EXAMPLE 12

Orientation of Melt-Spun Monofilaments

Polymers of Examples 7 through 10 that had been extruded as described in Example 11 were oriented by two-stage drawing into monofilament sutures. Prior to drawing Example 7, monofilaments were pre-tensioned and annealed. The drawing was conducted at 90–100° C. in the first stage and 100–130° C. in the second stage. The overall draw ratio varied between 3.73× and 4.6×. A number of monofilaments were relaxed at 70° C. for 15 minutes to reduce their free shrinkage. Properties of the oriented monofilaments are summarized in Table I.

TABLE I

Drawing Conditions and Fiber Properties of Polymers from Examples 7 through 9

| Origin of Extruded Polymer | Fiber Number | Draw Ratio | Draw Temp. (S1/S2) | Pre-Draw Annealing (min/° C.) | Post-Draw Relaxation (%) | Free Shrinkage (%) | Diameter (mil) | Straight Strength (Kpsi) | Modulus (Kpsi) | Elongation (%) |
|---|---|---|---|---|---|---|---|---|---|---|
| Example 7 | 7F-1 | 3.73X | 95/130 | 35/65 | — | 4.4 | 13.4 | 75 | 444 | 22 |
| 7 | 7F-2 | 3.73X | 95/130 | 35/65 | 2.3 | 1.8 | 15.1 | 53 | 182 | 36 |
| 7 | 7F-3 | 4.14X | 95/120 | 30/65 | — | 4.2 | 10.2 | 66 | 434 | 19 |
| 7 | 7F-4 | 4.14X | 95/120 | 30/65 | 3 | 1.5 | 11.0 | 61 | 257 | 31 |
| 8 | 8F-1 | 4.50X | 100/120 | — | — | 3.1 | 10.2 | 71 | 195 | 26 |
| 9 | 9F-1 | 4.43X | 100/130 | — | — | 2.1 | 10.6 | 72 | 230 | 27 |
| 10 | 10F-1 | 4.60X | 95/120 | — | — | 2.4 | 12.6 | 57 | 158 | 25 |

EXAMPLE 13

Sterilization of Monofilament Sutures and Evaluation of their In Vitro Breaking Strength Retention Monofilament sutures Numbers 8F-1 and 9F-1 described in Table I were radiochemically sterilized in hermetically sealed foil packages that have been pre-purged with dry nitrogen gas, using 5 and 7.5 KGy of gamma radiation. The radiochemical sterilization process entails the use of 200–400 mg of Delrin (poly-formaldehyde) film as package inserts for the controlled release, radiolytically, of formaldehyde gas as described earlier by Correa et al., [Sixth World Biomaterials Congress, *Trans Soc. Biomat., II*, 992 (2000)]. The sterile monofilament sutures were incubated in a phosphate buffer at 37° C. and pH=7.4 to determine their breaking strength retention profile as absorbable sutures. Using the breaking strength data of non-sterile sutures (Table I), the breaking strength retention data of sterile sutures were calculated. A summary of these data is given in Table II. These data indicate all sutures retained measurable strength at two weeks in the buffer solution.

TABLE II

Tensile Properties and In Vitro Breaking Strength Retention (BSR) of Radiochemically Sterilized Monofilament Sutures

| | Suture Number | | | |
|---|---|---|---|---|
| | 9F-1 | | 8F-1 | |
| Sterilization Dose (KGy) | 5 | 7.5 | 5 | 7.5 |
| Post-irradiation Tensile Properties | | | | |
| Tensile Strength (Kpsi) | 66 | 68 | 67 | 65 |
| Modulus (Kpsi) | 266 | 254 | 269 | 263 |
| Elongation (Kpsi) | 30 | 35 | 31 | 30 |
| BSR, % at | | | | |
| Week 1 | 70 | 57 | 82 | 72 |
| Week 2 | 24 | 22 | 18 | 17 |

EXAMPLE 14

Synthesis of 21/30/4 (Molar) Caprolactone/Trimethylene Carbonate as a Triaxial Initiator and Reaction with 40/5 Relative Molar Parts of 1-Lactide/Caprolactone Glycolide (22.74 g, 0.2 mole), TMC (149.94 g, 1.47 mole), caprolactone (117.31 g, 1.03 mole), triethanolamine (1.34 g, 9 mmole), and stannous octoate (3.86×10$^{-4}$ mole as 0.2 M solution in toluene) were reacted in similar equipment and environment as those described in Example 7. The formation of the triaxial initiator was completed after heating at 180° C. for 160 minutes. The product was cooled to room temperature and a mixture of 1-lactide (282.24 g., 1.96 mole) and caprolactone (27.93 g, 0.25 mole) were added under nitrogen atmosphere. The reactants were prepared for the second step of polymerization as described in Example 7. And the final polymer formation was completed after heating between 195–200° C. for 15 minutes until complete dissolution of triaxial initiator, and then heating for 23 hours at 140° C. The polymer was isolated, ground, dried, and heated under reduced pressure to remove residual monomer. The polymer was characterized by NMR and IR (for identity), DSC for thermal transition ($T_m$=148° C., $\Delta H$=19 J/g), and inherent viscometry (I.V.) in chloroform (for molecular weight, I.V.=1.14 dL/g).

EXAMPLE 15

Synthesis of 156/20 (Molar) Caprolactone/Trimethylene Carbonate Copolymer as Triaxial Initiator and Reaction with Relative 65 Molar Parts Glycolide Using a similar scheme to that used in Example 7, the triaxial initiator was prepared using caprolactone (45.5 g, 0.399 mole), TMC (54.3 g, 0.532 mole), trimethylolpropane (0.713 g, 5.32 mmole) and stannous octoate (5.32×10$^{-5}$ mole as a 0.2 M solution in toluene) and a polymerization temperature and time of 160° C./5 hours. As in Example 7, glycolide (200.6 g, 1.729 mole) was allowed to end-graft onto the triaxial initiator in presence of D & C Violet #2 (0.5 g) at 180° C./5 hours. The polymer was isolated, purified, and characterized as in Example 7. It had an inherent viscosity in HFIP=0.66 dL/g, $T_m$=225° C., $\Delta H$=66 J/g.

EXAMPLE 16

Processing of Example 15 Copolymer into Monofilaments and Evaluation of Their Properties Following a similar processing scheme to those used for the copolymer of Example 7 (as described in Examples 11 and 12), the respective monofilaments of Example 15 were produced and exhibited the following properties:

$T_m$–214° C., $\Delta H$=64 J/g

The DSC thermogram showed a minor endothermic transition at about 65° C.

Fiber Diameter=0.28 mm

Straight tensile strength=76 Kpsi

Modulus=335 Kpsi
Elongation=42%

The monofilaments were examined for breaking strength retention (BSR) after incubation in a phosphate buffer at 37° C. and pH=7.4. The percent BSR at one and two weeks was 72 and 24, respectively.

EXAMPLE 17

Synthesis of 15/20 (Molar) Caprolactone/Trimethylene Carbonate Copolymer as Triaxial Initiator and Reaction with Relative 65 Molar Parts Glycolide The triaxial initiator was prepared as in Example 15 with the exception of using (1) Triethanolamine as the monomeric initiator; (stannous octoate at ~30% higher concentration; and (3) reaction time of 18 hours. End-grafting with glycolide was carried out as in Example 15. The purified polymer was shown to have inherent viscosity=0.94 dL/g, $T_m$=220° C., and ΔH=81.1 J/g.

EXAMPLE 18

Processing of Example 17 Copolymer into Monofilaments and Evaluation of Their Properties A monofilament suture was prepared from the copolymer of Example 17 and oriented following a similar scheme to that used in Example 16. The monofilaments exhibited the following properties:
 $T_m$–214° C., ΔH=53 J/g A minor endothermic transition was observed in partially and fully oriented monofilament at about 60° C. and 90° C., respectively.
 Fiber Diameter=0.29 mm
 Straight tensile strength=78 Kpsi
 Modulus=296 Kpsi
 Elongation=58%

The monofilaments were examined for breaking strength retention at incubation in a phosphate buffer at 37° C. and pH=7.4. The percent BSR at one and two weeks was 78 and 51, respectively. In addition to the oriented monofilament described above, the copolymer of example 17 was extruded into microfilaments having a diameter of 60–120μ. These were used without additional orientation in composite assembling as described in Example 19. These microfilaments displayed an elongation that exceeded 300%.

EXAMPLE 19

General Method for Assembling Composite Stent Mantle

The undrawn microfilaments from Example 18 were wrapped in two opposite directions on a Teflon rod having a diameter of 2–4 mm to provide a two-component, cross-spiral construct. Each constituent spiral was comprised of 1 to 10 turns/cm along the axis of the Teflon rod. While on the Teflon rod, the cross-spiral construct was coated with a solution (10–20% in dichloromethane, DCM) of the copolymer of Example 14. The coating process entails multiple steps of dipping and air-drying and was pursued until the desirable coating thickness is achieved (25–50μ). Complete removal of the solvent was achieved by replacing the composite on the Teflon rod under reduced pressure at 25° C. for 6–12 hours until a constant weight is realized. The composite tube (typically 2–5 cm long) was removed from the Teflon cylinder by gentle sliding. This was then cut to the desired length before sliding over a metallic stent.

As indicated above a number of different applications for the copolymer exist. Below two specific applications, namely a device for sealing punctured blood vessels and a stent, will be described more thoroughly.

Figure 2:
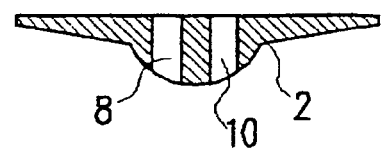
FIG. 2 shows a sectional view of a first sealing member.

FIG. 1 shows a sealing device for closing a wound in a wall of a vessel according to a first embodiment of the invention. The sealing device comprises three separate parts, namely a first sealing member 2 an elongated member 4 and a second sealing member 6. The first sealing member 2 is attached to a distal end of the elongate member 4. In this first embodiment of the sealing device, the first sealing member comprises two through openings 8, 10 (FIG. 2) through which a multifilament suture wire 12 is thread so as to make a pair of suture wires constituting the elongated member 4.

Figure 3:
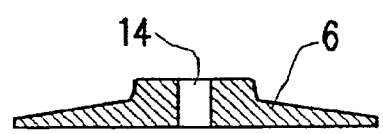
FIG. 3 shows a sectional view of a second sealing member.
Figure 4:
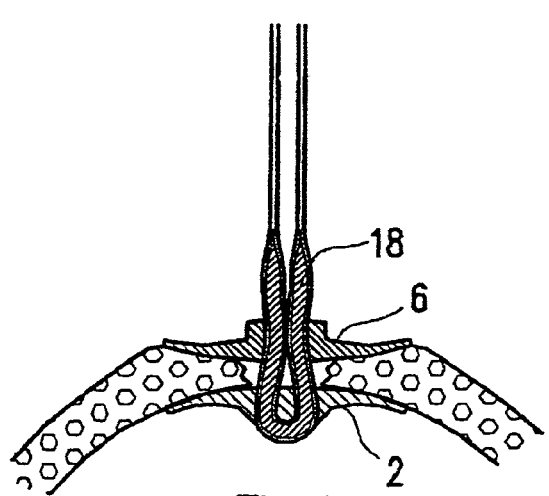
FIG. 4 shows a sealing device for closing a wound in a wall of a vessel according to a first embodiment of a first specific application of the invention.

The second sealing member 6 is provided with an opening 14 (FIG. 3), which is adapted to the elongate member 4, i.e. the opening 14 is greater than the thickness of the proximal portion of the elongate member 4. With a structure like this the second sealing member 6 is threadable onto and along the elongate element 4 (FIG. 1). The most distal portion of the elongate member 4 has a constant thickness that is slightly greater than the opening 14 of the second sealing member 6 and constitutes the distal lock portion 16. This will allow for frictional engagement between inside of the opening 14 of the second sealing member 6 and the distal lock portion 16 of the elongate member 4 which makes the sealing device infinitely variable lockable along said distal lock portion 16 (FIG. 4).

The multifilament suture wire 12 is preferably made of a resorbable material such as glycolic/lactide polymer The first sealing member 2 and second sealing member 6 are made of the flexible resorbable copolymer, preferably the present inventive copolymer.

The choice of using a suture wire for the elongated element 4 is very important for the security of the sealing device. It is within the scope of the present invention, but less preferred, to use the same material, e.g. a polymer, in the elongated member 4 as in the second sealing member 6. Since polymer gives a very glossy surface, it is hard to get high power frictional engagement between the elongated member 4 and the sealing member 6. Using a suture wire 12 or braided suture for the elongate member 4 gives a safer sealing since the suture wire comprises a number of circulating fibres thus giving the wire a rough surface with a high frictional sealing power towards a glossy surface inside the opening 14 of the second sealing member 6.

The suture wire also makes the sealing device safer in another way. The suture wire is made in one piece and has very high tensile strength. It constitutes a continuous wire from the inner seal through the outer seal and to a tampering grip of the insertion tool, being threaded in through the first opening 8 and out again through the second opening 10 and thus keeping the sealing device safe together. If a first sealing member and an elongated member are cast in one piece there is often problem with the casting process, giving the casted member air bubbles and inclusions and accordingly giving the sealing device poor structural strength. The challenge is to make the suture wire 12 thicker in the distal lock portion 16.

Figure 5:
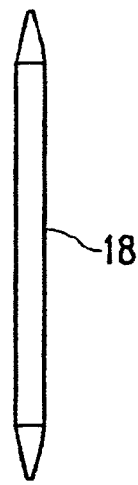
FIG. 5 shows an elongated core.

In the first embodiment of the present invention, a hollow core of the suture wire sheath is filled with a less flexible filament core 18 (FIG. 5), within the area of the distal lock portion 16 of the elongate member 4, but also in the area which is to be threaded through the first sealing member 2. (See again FIG. 1). The elongated core 18 is preferably made of an absorbable copolymer in accordance with the present invention. This gives the suture wire 12 a thickening in the distal lock portion 16.

In a second embodiment of the present invention, shown in FIG. 6, the suture wire 12 is left unfilled within the area ranging from the entry of the first opening 8 of the first sealing member 2, through the first sealing member 2, out on the on the other side and in again through the second opening 10 of the first sealing member 2 to the exit of said second opening 10.

In a third embodiment of the present invention, shown in FIG. 7, the thickening of the first suture, of the two sutures making a pair of sutures, extends beyond the distal lock portion 16 into the proximal portion of the elongated member 4. This gives the suture wire 12 a more continuous increasing of the thickness which simplifies the threading of the second sealing member 6 from the proximal portion onto the distal lock portion 16.

In a fourth embodiment of the present invention, instead of being filled, the suture 12 is thicker woven in the area of the distal lock portion.

In a fifth embodiment of the present invention, (FIGS. 8 and 9) the second sealing member is divided into two parts, which first part 41 is a plate and is provided with an opening that is approximately the same or slightly grater than thickness of the distal lock portion 16. This first part 41 is threadable onto and along the elongate member 4 (FIG. 8), over the distal lock portion until it is in contact with the outside of the vessel wall. The first part plate 41 is preferably quite thin, which makes it flexible and easy to adapt to the Vessel wall. The second part 42 is provided with an opening that is slightly smaller than the thickness of the distal lock portion 16. This second part 42 is threadable onto and along the elongate member 4 (FIG. 8), over the distal lock portion until it is in contact with the first part 41. The second part 42 allows for frictional engagement between the inside of the opening of the second part 42 and the distal portion 16 (FIG. 9). The second part 42 is preferably thicker than the first part 41, which will give it a large surface inside its opening for said frictional engagement. On the other hand, the diameter of the second part 42 is preferably smaller than that of the first part 41.

In a sixth embodiment, the elongated portion 4 is not a suture wire, but another material, e.g. a resorbable polymer. The distal lock portion 16 is coated by a hollow, stocking-like suture wire so that a decent frictional engagement can be achieved between said coated distal lock portion and the inside of the opening of the second sealing member.

Figure 10:
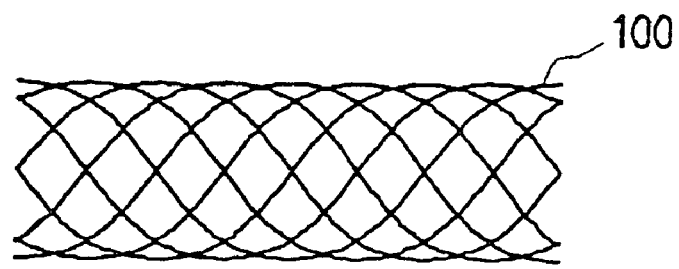
FIG. 10 shows schematically a prior art stent applicable in the present invention.

As mentioned above, the subject copolymers may be converted to a highly compliant, expandable tubular mantle, sleeve or cover that is placed tightly outside an expandable metallic or polymeric stent so that under concentric irreversible expansion at the desired site of a treated biological conduit, such as blood vessel or a urethra, both components will simultaneously expand and the mantle provides a barrier between the inner wall of the conduit and the outer wall of the stent. In another aspect of this invention, the subject copolymers are used as a stretchable matrix of a fiber-reinforced cover, sleeve, or mantle for a stent, wherein the fiber reinforcement is in the form of spirally coiled yarn (with or without crimping) woven, knitted, or braided construct. FIG. 10 shows schematically a radially expandable prior art spirally coiled metal stent which is applicable in the present invention.

Figure 11:
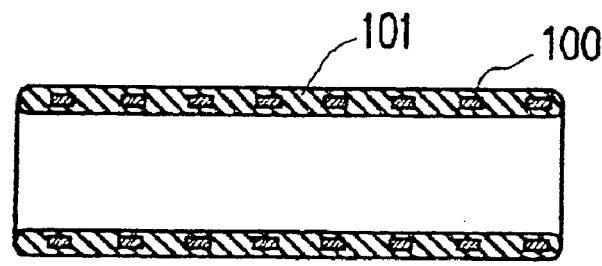
FIG. 11 is a longitudinal view of a stent according to a preferred embodiment of the present invention.

FIG. 11 is a longitudinal view of a stent where the metal stent 100 is completely covered by the subject copolymer 101 according to a preferred embodiment of the present invention.

Figure 12:
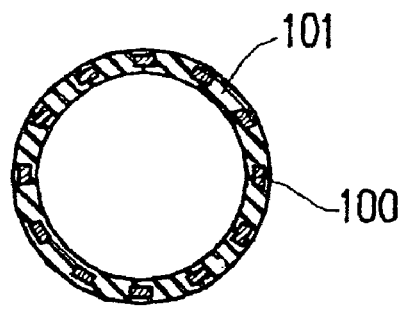
FIG. 12 is a cross sectional view of the stent shown in FIG. 11.

FIG. 12 is a cross sectional view of the stent shown in FIG. 11.

Figure 13:
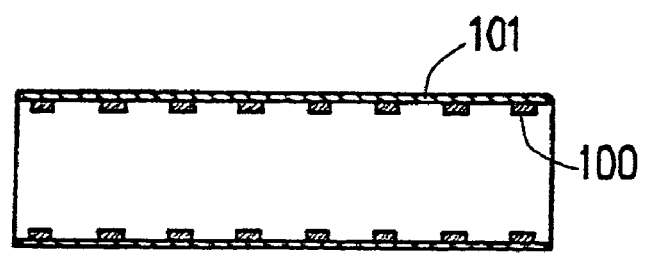
FIG. 13 is a longitudinal view of a stent according to another preferred embodiment of the present invention.

FIG. 13 is a longitudinal view of a stent where the outer surface is covered by the subject copolymer 101 according to another preferred embodiment of the present invention. The size of a stent depends naturally of the intended use, i.e. the dimensions of the vessel where it should be applied. Typical coronary stent dimensions may have a pre deployment outer diameter of 1.6 mm and an expanded outer diameter of 3.0 mm to 4.5 mm. The length is preferably 15 mm or 28 mm.

Although the present invention has been described in connection with the preferred embodiments, it is to be understood that modifications and variations may be utilized without departing from the principles and scope of the invention, as those skilled in the art will readily understand. Accordingly, such modifications may be practised within the scope of the following claims. Moreover, Applicants hereby disclose all subranges of all ranges disclosed herein. These subranges are also useful in carrying out the present invention.

What is claimed is:

1. A composite tubular cover or mantle for a stent comprising a polymeric matrix reinforced with monofilament cross-spirals, wherein at least one of the matrix and the reinforcement comprise an absorbable, crystalline, monocentric, polyaxial copolymer comprising:
   a central atom selected from the group consisting of carbon and nitrogen; and
   at least three axes originating and extending outwardly from the central atom, each axis comprising:
      an amorphous, flexible component adjacent to and originating from the central atom, the amorphous component comprising repeat units derived from at least one cyclic monomer selected from the group consisting essentially of carbonates and lactones; and
      a rigid, crystallizable component extending outwardly from the amorphous, flexible component, the crystallizable component comprising repeat units derived from at least one lactone;
   wherein the copolymer comprises a melting temperature greater than 120° C., a heat of fusion greater than 10 J/g, and an endothermic transition at 40–100° C., wherein the endothermic transition can be controlled by subsequent heat treatment of the copolymer.

2. The composite tubular cover or mantle for a stent set forth in claim 1 wherein the subsequent heat treatment comprises orientation.

3. The composite tubular cover or mantle for a stent set forth in claim 1 wherein the subsequent heat treatment comprises annealing above 250° C.

4. The composite tubular cover or mantle for a stent set forth in claim 1 wherein the crystallizable component comprises repeat units derived from l-lactide.

5. The composite tubular cover or mantle for a stent set forth in claim 1 wherein the crystallizable component comprises repeat units derived from glycolide.

6. The composite tubular cover or mantle for a stent set forth in claim 4 wherein the crystallizable component comprises repeat units derived from a second monomer selected from the group consisting of trimethylene carbonate, caprolactone, p-dioxanone, and 1,5-dioxepan-2-one.

7. The composite tubular cover or mantle for a stent set forth in claim 5 wherein the crystallizable component comprises repeat units derived from a second monomer selected from the group consisting of trimethylene carbonate, caprolactone, p-dioxanone, and 1,5-dioxepan-2-one.

* * * * *